United States Patent
Elsas, II et al.

(10) Patent No.: US 6,207,387 B1
(45) Date of Patent: Mar. 27, 2001

(54) MOLECULAR DIAGNOSTICS FOR GALACTOSEMIA

(75) Inventors: Louis J. Elsas, II; Kasinathan Muralidharan, both of Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/413,304

(22) Filed: Oct. 6, 1999

Related U.S. Application Data

(60) Provisional application No. 60/103,286, filed on Oct. 6, 1998.

(51) Int. Cl.[7] ............................................. C12Q 1/68
(52) U.S. Cl. ......................... 435/6; 435/91.2; 536/23.5; 536/24.31; 536/24.33
(58) Field of Search ................... 435/6, 91.2; 536/23.5, 536/24.31, 24.33

(56) References Cited

PUBLICATIONS

Reichardt et al. Genomics 12(3)596–300 (1992).*
Reichardt et al. PNAS (1991) 88:2633–2637.*
Elsas. GenBank Accession No. L48720. 1995.*
GenBank Accession No. L46363. 1995.*
GenBank Accession No. L46699. 1995.*
GenBank Accession No. L46704. 1995.*
GenBank Accession No. L46708. 1995.*
GenBank Accession No. L46711. 1995.*
Sambrook et al. Molecular Cloning. Cold Spring Harbor Laboratory Press, 1989, p. 11.48–11.49.*
Ririe et al. Analytical Biochemistry 245, 154–160 (1997).*
Lai et al. "Duarte Allele Impairs Biostability of Galactos–1–Phosphate Uridyltransferase in Human Lymphoblasts" Human Mutation 11:28–38, 1998.
Langley et al. "Molecular Basis for Duarte and Los Angeles Variant Galactosemia" Am. J. Hum. Genet. 60:366–372, 1997.
Elsas et al. "Molecular Support for Newborn Galactosemia Screening" Presentation May 22–23, 1997, Third Meeting of the International Society for Neonatal Screening, IKON Map, Boston, p. 7–12.
Lai et al. "A Prevalent Mutation for Galactosemia among Black Americans" J. of Pedr., 128(1):89–95 Jan., 1996.
Lin et al. "Multiplex Genotype Determination at a Large No. of Gene Loci" Proc. Natl. Acad. Sci., 93:2582–2587, Mar., 1996.
Melchior, Jr. et al. "Alteration of the Relative Stability of dA • dT and dG • dC Base Pairs in DNA" PNAS 70(2):298–302, Feb., 1973.
Wittwer et al. "Continuous Fluorescence Monitoring of Rapid Cycle DNA Amplification" BioTechniques 22:130–131, 134–136, 138, Jan. 1997 (advertising pages excluded).
Wittwer et al. "The LightCycler™: A Microvolume Multi-sample Fluorimeter with Rapid Temperature Control" Bio-Techniques 22(1):176–181, Jan., 1997.
Berry et al. "In Vivo Oxidation of [$^{13}$C]Galactose in Patients with Galactose–1–Phosphate Uridyltransferase Deficiency" Biochem. and Molecular Med. 56:158–165, 1995.
GenBank Accession No. M96264, 1995.
Elsas et al. "Galactosemia: A Strategy to Identify New Biochemical Phenotypes and Molecular Genotypes" Am J. Hum. Genet. 56:630–639, 1995.
Elsas et al. "A Common Mutation Associated with the Duarte Galactosemia Allele" Am. J. Hum. Genet. 54:1030–1036, 1994.
Elsas et al. "Galactosemia A Molecular Approach to the Enigma" Internet. Pediatr., 8(1):101–109, 1993.
Waggoner et al. "Long–term Complications in Treated Galactosemia" Internet. Pediatr., 8(1):97–100, 1993.
Leslie et al. "The Human Galactose–1–phosphate Uridyl-transferase Gene" Genomics 14:474–480, 1992.
Reichardt et al. "Molecular Characterization of Two Galactosemia Mutations: Correlation of Mutations with Highly Conserved Domains in Galactose–1–Phosphate Uridyl Transferase" Am. J. Hum. Genet. 49:860–867, 1991.
Nickerson et al. "Automated DNA Diagnostics using an ELISA–based Oligonucleotide Ligation Assay" Proc. Natl. Acad. Sci., 87:8923–8927, Nov. 1990.
Flach et al. "Sequence of a cDNA Encoding Human Galactose–1–Phosphate Uridyl Transferase" Mol. Biol. Med., 7:365–369, 1990.
Waggoner et al. "Long–term Prognosis in Galactosaemia: Results of a Survey of 350 Cases" J. Inher. Metab. Dis., 13:802–818, 1990.

* cited by examiner

*Primary Examiner*—Jeffrey Fredman
*Assistant Examiner*—Juliet C Einsmann
(74) *Attorney, Agent, or Firm*—Needle & Rosenberg, P.C.

(57) ABSTRACT

A process for detecting mutations in the gene responsible for galactosemia, galactose-1-phosphate uridyl transferase (GALT), is described. In one embodiment, the process can be used to detect over 85% of the mutations known to cause galactosemia in the United States population by using six different oligonucleotide probes, which span single-nucleotide Missense or nonsense mutations in the GALT gene. Hybridization conditions which can distinguish a single nucleotide mismatch are used to detect both the presence and zygosity of mutations in the GALT gene to aid in genetic counseling. A kit for use in detecting mutations in the GALT gene is also disclosed.

11 Claims, No Drawings

SEQUENCE LISTING

<160> NUMBER OF SEQ ID NOS: 15

<210> SEQ ID NO 1
<211> LENGTH: 21
<212> TYPE: DNA
<213> ORGANISM: Homo sapiens

<400> SEQUENCE: 1
cacccctggt tggatgtaac g                                    21

<210> SEQ ID NO 2
<211> LENGTH: 21
<212> TYPE: DNA
<213> ORGANISM: Homo sapiens
<220> FEATURE:
<223> OTHER INFORMATION: Description of Artificial Sequence:/Note =

<400> SEQUENCE: 2
ccccactgcc gggtaagggt g                                    21

<210> SEQ ID NO 3
<211> LENGTH: 21
<212> TYPE: DNA
<213> ORGANISM: Homo sapiens
<220> FEATURE:
<223> OTHER INFORMATION: Description of Artificial Sequence:/Note =

<400> SEQUENCE: 3
agcagtttcc cgccagatat t                                    21

<210> SEQ ID NO 4
<211> LENGTH: 21
<212> TYPE: DNA
<213> ORGANISM: Homo sapiens
<220> FEATURE:
<223> OTHER INFORMATION: Description of Artificial Sequence:/Note =

<400> SEQUENCE: 4
tcttgaccaa ttatgacaac c                                    21

<210> SEQ ID NO 5
<211> LENGTH: 21
<212> TYPE: DNA

-continued

```
<213> ORGANISM: Homo sapiens
<220> FEATURE:
<223> OTHER INFORMATION: Description of Artificial Sequence:/Note =

<400> SEQUENCE: 5
ggccaactgg gaccattggc a                                              21

<210> SEQ ID NO 6
<211> LENGTH: 21
<212> TYPE: DNA
<213> ORGANISM: Homo sapiens
<220> FEATURE:
<223> OTHER INFORMATION: Description of Artificial Sequence:/Note =

<400> SEQUENCE: 6
cagcaggcct gtaagagtca g                                              21

<210> SEQ ID NO 7
<211> LENGTH: 4286
<212> TYPE: DNA
<213> ORGANISM: Homo sapiens
<220> FEATURE:
<223> OTHER INFORMATION: Description of Artificial Sequence:/Note =

<400> SEQUENCE: 7
gaattccgga tcaaatgaat gattgcagca agcaagtcct gtaggcatcc tggagcccaa      60
ggattctgca gtaggcagct ttcacagagg ttcttccagt gtagtggctc tagctctggg     120
tgaagtagga tcatcaatgt cggccccag ggttcacagc tgttctgagc cccgccccct     180
ggtggcagcc gacgggagtc agtcagtcac gtgctggcgg ctggccaatc atcgggggcg     240
gcgcggggag gggtggtgtg gacggagaaa gtgaaaggtg aggcacggcc ctgcagattt     300
tccagcggat cccccggtgg cctcatgtcg cgcagtggaa ccgatcctca gcaacgccag     360
caggcgtcag aggcggacgc cgcagcagca accttccggg caaacggtaa ctgcaccgcg     420
gcagggactc gctgggcgc ggagccgagc cctccccttc cttaggaagc tttcgtcccc     480
ctccgaaggt tggaacgctc atcccgagcc agaccgacaa ggcgtacagt ctgcaggcct     540
ctacgagcag caggccaatt ggcgctggga aagtccaatc ctgggcctct agctcctgag     600
cgggacaggg ccgagagggc gctcccgagc ttgggcctgc tggtgggtga acccaggag     660 agagggagct agaggggga gctctgagga ctgatcttga ctgtctgccc ccagaccatc     720
agcatatccg ctacaacccg ctgcaggatg agtgggtgct ggtgtcagct caccgcatga     780
agcggccctg gcagggtcaa gtggagcccc agcttctgaa gacagtgccc cgccatgacc     840
ctctcaaccc tctgtgtcct ggggccatcc gagccaacgg agaggtaagc ctgtagagcc     900
ctgcatctgc aggctgggcc acggggagta gttccctctt agaactgtcc tccacccaca     960
ggatagtgaa cctccttctg ggtcatatcc caccaagctt tttggtcccc tagggtgggc    1020
cttccctact cccttgtagc ctgtccagtc tttgaagccc accaggtaac tggtggtatg    1080
gggcagtgag tgcttctagc ctatccttgt cggtaggtga atccccagta cgatagcacc    1140
ttcctgtttg acaacgactt cccagctctg cagcctgatg ccccccagtcc aggtaacctg    1200 gctccaactg ctgctgggga ggagggtggc tagacctctt gagggacttc tgctgcagag    1260
atgctgagtg atactccttt acctcaggac ccagtgatca tccccttttc caagcaaagt    1320
ctgctcgagg agtctggtaa ctatggattt cccctcttac aactttcaaa ccagagttgg    1380
agactcagca ttgggttcg ccctgccgt agcacagcca agccctacct ctcggttatc    1440
ttttctcccg tcaccaccca gtaaggtcat gtgcttccac ccctggtcgg atgtaacgct    1500
```

```
gccactcatg tcggtccctg agatccgggc tgttgttgat gcatgggcct cagtcacaga    1560
ggagctgggt gcccagtacc cttgggtgca ggtttgtgag gtcgccccct cccctggatg    1620
ggcagggagg gggtgatgaa gctttggttc tggggagtaa catttctgtt tccacagggt    1680
gtggtcagga gggagttgac ttggtgtctt ttggctaaca gagctccgta tccctatctg    1740
atagatcttt gaaaacaaag gtgccatgat gggctgttct aacccccacc cccactgcca    1800
ggtaagggtg tcaggggctc cagtgggttt cttggctgag tctgagccag cactgtggac    1860
atgggaacag gattaatgga tgggacagag gaaatatgcc aatgatgtgg aggcttggag    1920
gtaaaggacc tgcctgttct tctctgcttt tgcccccttga caggtatggg ccagcagttt    1980
cctgccagat attgcccagc gtgaggagcg atctcagcag gcctataaga gtcagcatgg    2040
agagcccctg ctaatggagt acagccgcca ggagctactc aggaaggtgg agagagcca    2100 agccctgtgt ccccaaggag tccctaactt tcttatccca tgagagagt gtgtaaagga    2160 gaaagctaga ggtgaactag tagagagaga cttgctagga ggccttagca ataatccagt    2220
aatctaaagg aaagatgatg gtgacttaga ctccgggtggt tagtggtaga ggtggtgaga    2280
agacatcaga tcctgggcac attcttttct tctgcttccc ttgcctattt gctgaccaca    2340
ctccggctcc tatgtcacct tgatgacttc ctatccattc tgtcttccta ggaacgtctg    2400
gtcctaacca gtgagcactg gttagtactg gtccccttct gggcaacatg gccctaccag    2460
acactgctgc tgccccgtcg gcatgtgcgg cggctacctg agctgacccc tgctgagcgt    2520
gatggtcagt ctcccaagta ggatcctggg gctaggcact ggatggaggt tgctcccagt    2580
agggtcagca tctggacccc aggctgagag tcaggtctg attccagatc tagcctccat    2640
catgaagaag ctcttgacca agtatgacaa cctctttgag acgtcctttc cctactccat    2700
gggctggcat ggtgaggctt ttcaagtacc tatatttagc cccaacacca tttctgggct    2760
cctgggctca gcctagtgaa ctgcaacctc aaaggagcaa gccttgaaac agttgctggg    2820
ggaagtggcc agagtagaga tgctgggact gagggtggag cagcaaactt ggtgaaacta    2880
catctccaat gtgctttcta atctcctgcc agctcttctc aagcagggga tcctgggaga    2940
tgtagttttc agatacctgg ttgggtttgg gagtaggtgc taacctggat aactgtaaaa    3000
gggctctctc tcccccactgt ctctcttctt tctgtcaggg gctcccacag gatcagaggc    3060
tggggccaac tggaaccatt ggcagctgca cgctcattac taccctccgc tcctgcgctc    3120
tgccactgtc cggaaattca tggttggcta cgaaatgctt gctcaggctc agagggacct    3180 caccccctgag caggtcagga ctcagaacag tctggcgtct ccagactctc acatgcagta    3240
tgtgcaggca cctgatactt ctgttgccct tgtgctccaa tcattgcaca aggcagaaac    3300
agctctggca ggaagggact gccaaagtta ggagccctag gcctggaag gagagtatgg    3360 tcctcagatc cccttctct cctgcttcct ccagggaacc aacagtcat gaccctgata    3420 gtttcccata caacctggg cattccttgg gactcaggag ctgctaaact ctttcatccc    3480
ctggtggctt cagcagtcct tatcaccagc ctcacaatcc cacaggccca ccccagtgg    3540 gcctgtggca ttcatatttc atattcatat ttcaaccac aatatccagc aaaatgtctc    3600
ctgagcaccc agaactccat accatcggcc gggtgtggtg gctcatgcct taatcccagc    3660
actttgggag gtcaagatgg gaggattgct tgagcccaga agttcgagac tagcctggga    3720
aacataggaa gccctcgtct ctacaaaaaa aatttaaaaa gttagccagg tatggtggca    3780
tatacgatgc tttgtggtcc cagatacttg ggaggctgag ataggatcac ttgggcccag    3840
```

| | |
|---|---|
| gagtttgagg ctgcagtgag ccatcatcat ggcatcattg cattccagcc tgggcaacag | 3900 |
| agcaagacct cgtctcaaaa aaaaaaaaaa aaatgaagtc catgccacca ttcttggcag | 3960 |
| cccagcccttt atcctcctta attgctccct gtccctttc caggctgcag agagactaag | 4020 |
| ggcacttcct gaggttcatt accacctggg gcagaaggac agggagacag caaccatcgc | 4080 |
| ctgaccacgc cgaccacagg gccttgaatc cttttttgtt ttcaacagtc ttgctgaatt | 4140 |
| aagcagaaag ggccttgaat cctggcctgg aatttgggca gatatagcat taataaaact | 4200 |
| gtgcatctca aactttatc acatactcta atatcagagg agtgtgaacc ttcagagatc | 4260 |
| tagggttaaa agctaaaggc atagct | 4286 |

<210> SEQ ID NO 8
<211> LENGTH: 1617
<212> TYPE: DNA
<213> ORGANISM: Homo sapiens
<220> FEATURE:
<223> OTHER INFORMATION: Description of Artificial Sequence:/Note =

<400> SEQUENCE: 8

| | |
|---|---|
| taaggtcatg tgcttccacc cctggtcgga tgtaacgctg ccactcatgt cggtccctga | 60 |
| gatccgggct gttgttgatg catgggcctc agtcacagag gagctgggtg cccagtaccc | 120 |
| ttgggtgcag gtttgtgagg tcgccccttc ccctggatgg gcaggaggg ggtgatgaag | 180 |
| ctttggttct ggggagtaac atttctgttt ccacagggtg tggtcaggag ggagttgact | 240 |
| tggtgtcttt tggctaacag agctccgtat ccctatctga tagatctttg aaaacaaagg | 300 |
| tgccatgatg ggctgttcta acccccaccc ccactgccag gtaagggtgt caggggctcc | 360 |
| agtgggtttc ttggctgagt ctgagccagc actgtggaca tgggaacagg attaatggat | 420 |
| gggacagagg aaatatgcca atgatgtgga ggcttggagg taaaggacct gcctgttctt | 480 |
| ctctgctttt gccccttgac aggtatgggc cagcagtttc ctgccagata ttgcccagcg | 540 |
| tgaggagcga tctcagcagg cctataagag tcagcatgga gagcccctgc taatggagta | 600 |
| cagccgccag gagctactca ggaaggtggg agagagccaa gccctgtgtc cccaaggagt | 660 |
| ccctaacttt cttatcccat gagagaggtg tgtaaaggag aaagctagag gtgaactagt | 720 |
| agagagagac ttgctaggag gccttagcaa taatccagta atctaaagga aagatgatgg | 780 |
| tgacttagac tcgggtggtt agtggtagag gtggtgagaa gacatcagat cctgggcaca | 840 |
| ttcttttctt ctgcttccct tgcctatttg ctgaccacac tccggctcct atgtcacctt | 900 |
| gatgacttcc tatccattct gtcttcctag gaacgtctgg tcctaaccag tgagcactgg | 960 |
| ttagtactgg tccccttctg ggcaacatgg ccctaccaga cactgctgct gccccgtcgg | 1020 |
| catgtgcggc ggctacctga gctgacccct gctgagcgtg atggtcagtc tcccaagtag | 1080 |
| gatcctgggg ctaggcactg gatggaggtt gctcccagta gggtcagcat ctggacccca | 1140 |
| ggctgagagt caggctctga ttccagatct agcctccatc atgaagaagc tcttgaccaa | 1200 |
| gtatgacaac ctcttgaga cgtccttcc ctactccatg gctggcatg gtgaggcttt | 1260 |
| tcaagtacct atatttagcc ccaacaccat ttctgggctc ctgggctcag cctagtgaac | 1320 |
| tgcaacctca aaggagcaag ccttgaaaca gttgctgggg gaagtggcca gagtagagat | 1380 |
| gctgggactg agggtggagc agcaaacttg gtgaaactac atctccaatg tgctttctaa | 1440 |
| tctcctgcca gctcttctca agcagggggat cctgggagat gtagttttca gatacctggt | 1500 |
| tgggtttggg agtaggtgct aacctggata actgtaaaag ggctctctct ccccactgtc | 1560 |
| tctcttcttt ctgtcagggg ctcccacagg atcagaggct ggggccaact ggaacca | 1617 |

```
<210> SEQ ID NO 9
<211> LENGTH: 20
<212> TYPE: DNA
<213> ORGANISM: Homo sapiens
<220> FEATURE:
<223> OTHER INFORMATION: Description of Artificial Sequence:/Note =

<400> SEQUENCE: 9
tgtagtggct ctagctctgg                                                  20

<210> SEQ ID NO 10
<211> LENGTH: 21
<212> TYPE: DNA
<213> ORGANISM: Homo sapiens
<220> FEATURE:
<223> OTHER INFORMATION: Description of Artificial Sequence:/Note =

<400> SEQUENCE: 10
tatcagatag ggatacggag c                                                21

<210> SEQ ID NO 11
<211> LENGTH: 21
<212> TYPE: DNA
<213> ORGANISM: Homo sapiens
<220> FEATURE:
<223> OTHER INFORMATION: Description of Artificial Sequence:/Note =

<400> SEQUENCE: 11
gtcaggaggg agttgacttg g                                                21

<210> SEQ ID NO 12
<211> LENGTH: 21
<212> TYPE: DNA
<213> ORGANISM: Homo sapiens
<220> FEATURE:
<223> OTHER INFORMATION: Description of Artificial Sequence:/Note =

<400> SEQUENCE: 12
gcccttttac agttatccag g                                                21

<210> SEQ ID NO 13
<211> LENGTH: 21
<212> TYPE: DNA
<213> ORGANISM: Homo sapiens
<220> FEATURE:
<223> OTHER INFORMATION: Description of Artificial Sequence:/Note =

<400> SEQUENCE: 13
tcaagcaggg gatcctggga g                                                21

<210> SEQ ID NO 14
<211> LENGTH: 21
<212> TYPE: DNA
<213> ORGANISM: Homo sapiens
<220> FEATURE:
<223> OTHER INFORMATION: Description of Artificial Sequence:/Note =

<400> SEQUENCE: 14
atctctgaag gttcacactc c                                                21

<210> SEQ ID NO 15
<211> LENGTH: 379
<212> TYPE: PRT
<213> ORGANISM: Homo sapiens
<220> FEATURE:
```

<223> OTHER INFORMATION: Description of Artificial Sequence:/Note =

<400> SEQUENCE: 15

```
Met Ser Arg Ser Gly Thr Asp Pro Gln Gln Arg Gln Gln Ala Ser Glu
 1               5                  10                  15

Ala Asp Ala Ala Ala Thr Phe Arg Ala Asn Asp His Gln His Ile
                20                  25                  30

Arg Tyr Asn Pro Leu Gln Asp Glu Trp Val Leu Val Ser Ala His Arg
                35                  40                  45

Met Lys Arg Pro Trp Gln Gly Gln Val Glu Pro Gln Leu Leu Lys Thr
        50                  55                  60

Val Pro Arg His Asp Pro Leu Asn Pro Leu Cys Pro Gly Ala Ile Arg
65                  70                  75                  80

Ala Asn Gly Glu Val Asn Pro Gln Tyr Asp Ser Thr Phe Leu Phe Asp
                85                  90                  95

Asn Asp Phe Pro Ala Leu Gln Pro Asp Ala Pro Ser Pro Gly Pro Ser
                100                 105                 110

Asp His Pro Leu Phe Gln Ala Lys Ser Ala Arg Gly Val Cys Lys Val
                115                 120                 125

Met Cys Phe His Pro Trp Ser Asp Val Thr Leu Pro Leu Met Ser Val
        130                 135                 140

Pro Glu Ile Arg Ala Val Val Asp Ala Trp Ala Ser Val Thr Glu Glu
145                 150                 155                 160

Leu Gly Ala Gln Tyr Pro Trp Val Gln Ile Phe Glu Asn Lys Gly Ala
                165                 170                 175

Met Met Gly Cys Ser Asn Pro His Pro His Cys Gln Val Trp Ala Ser
        180                 185                 190

Ser Phe Leu Pro Asp Ile Ala Gln Arg Glu Glu Arg Ser Gln Gln Ala
                195                 200                 205

Tyr Lys Ser Gln His Gly Glu Pro Leu Leu Met Glu Tyr Ser Arg Gln
        210                 215                 220

Glu Leu Leu Arg Lys Glu Arg Leu Val Leu Thr Ser Glu His Trp Leu
225                 230                 235                 240

Val Leu Val Pro Phe Trp Ala Thr Trp Pro Tyr Gln Thr Leu Leu Leu
                245                 250                 255

Pro Arg Arg His Val Arg Arg Leu Pro Glu Leu Thr Pro Ala Glu Arg
                260                 265                 270

Asp Asp Leu Ala Ser Ile Met Lys Lys Leu Leu Thr Lys Tyr Asp Asn
                275                 280                 285

Leu Phe Glu Thr Ser Phe Pro Tyr Ser Met Gly Trp His Gly Ala Pro
        290                 295                 300

Thr Gly Ser Glu Ala Gly Ala Asn Trp Asn His Trp Gln Leu His Ala
305                 310                 315                 320

His Tyr Tyr Pro Pro Leu Leu Arg Ser Ala Thr Val Arg Lys Phe Met
                325                 330                 335

Val Gly Tyr Glu Met Leu Ala Gln Ala Gln Arg Asp Leu Thr Pro Glu
                340                 345                 350

Gln Ala Ala Glu Arg Leu Arg Ala Leu Pro Glu Val His Tyr His Leu
                355                 360                 365

Gly Gln Lys Asp Arg Glu Thr Ala Thr Ile Ala
        370                 375
```

MOLECULAR DIAGNOSTICS FOR GALACTOSEMIA

This application claims priority in U.S. Provisional Application No. 60/103,286 filed Oct. 6, 1998.

The government may have certain rights in this invention, which was funded in part by National Institute of Child Health and Human Development Grant PO-1 HD 29847-01 and U.S. Public Health Services Grant M01-RR00039.

FIELD OF THE INVENTION

The field of this invention is the diagnosis of galactosemia using nucleic acid-based techniques.

BACKGROUND OF THE INVENTION

Galactosemia, an inherited metabolic disorder of milk sugar metabolism, is caused by certain mutations in the gene coding for the enzyme, galactose-1-phosphate uridyl transferase (GALT), which result in defective enzyme activity. This disorder is potentially fatal, so newborns throughout the U.S. and developed countries are screened for galactosemia, which when detected and treated early, saves lives and money. Evaluation of outcome in galactosemic patients began in the 1980s, and by 1990, an enigma was revealed (for example, see Kornrower, G M, *J. Inher. Metab. Dis.*, 1982, 5:96–104; Waggoner and Buist, 1993, *Internat. Pediatr.* 8:97–100). Although neonatal infants were screened and treated within days of life with a galactose-restricted diet, older children had unexpectedly poor outcomes. Dysfunctions included ovarian failure, verbal dyspraxia, growth and developmental delays, and neurological signs of cortical and extrapyramidal tract impairment. Since the GALT enzyme structure is highly conserved throughout evolution, the human GALT cDNA was cloned using probes homologous to known sequences in the bacterial enzyme. When the human cDNA and gene were sequenced (see Flach, Reichardt, and Elsas, 1990, Mol. Biol. Med. 7:365–369; and Leslie et al. 1992, Genomics 14:474–480), the first mutations in the GALT gene were associated with human galactosemia (Reichardt et al. 1991, Am. J. Hum. Genet. 49:860–867; Reichardt et al, 1992, Genomics 12: 596–600) and relationships between the mutations and the resulting phenotype were being reported (Elsas et al. 1993, Internat Pediatr. 8:101). The Q188R mutation, first reported in 1991, is the most common mutation among galactosemic patients of Caucasian ethnicity (Reichert et al. 1991, Ibid.) and causes a complete loss in GALT activity. The S135L mutation is common among African-Americans (Lai et al., J. Pediatr 1996, 128: 89–95), and results in severe reduction in GALT activity. The N314D mutation, also known as the Duarte allele (Elsas et al., 1994, Am J. Hum Genet 54: 1030–1036), causes an instability in the GALT protein that leads to a 50% reduction in activity in homozygous patients. The K285N mutation is the second most common mutation among white galactosemic patients, and is the most prevalent among patients in southern Germany and Austria (Leslie et al., 1992, Ibid.). Other common mutations identified in the white population are R148W and L195P (Reichart et al. 1992, Ibid.).

These reports led to the realizations that different GALT mutations can result in different phenotypes and that therapy recommendations may vary depending on the specific mutation.

Methods currently used in newborn screening determine only the level of enzymatic activity or the accumulation of precursors. Results from current techniques are altered by the sampling parameters, such as ambient temperature and time of feeding relative to collection of sample. Also, they do not reveal the specific mutations that cause the change in enzyme activity. Certain mutations cause a mild disease, while others cause severe effects. Identifying the mutation is necessary to make a diagnosis, initiate appropriate therapy, estimate prognosis, and provide appropriate genetic counseling for the family.

There remains a need for a test with increased sensitivity and specificity for screening and diagnosis of galactosemia and asymptomatic carriers of galactosemia. There is a need for a test that can be run simultaneously on a large number of samples, such as in a micro titer plate format now commonly in use in clinical diagnostic laboratories. There is a need for a testing protocol that can quickly and specifically identify the majority of the alleles that can contribute to galactosemia in the human populations.

The claimed invention describes a nucleic acid-based method that can detect and specify the mutation involved in over 85% of individuals with some form of galactosemia rapidly and economically. Such a screen would be applicable to universal newborn screening and should supplement or completely replace current screening strategies. The screen can also be used to detect heterozygous mutations and the presence of multiple mutations in the GALT gene, which are necessary for understanding and counseling heritability and recurrence risks to family members.

SUMMARY OF INVENTION

The invention as claimed is a nucleic acid-based method that can detect and specify the mutation involved in the great majority of individuals with some form of galactosemia rapidly and economically. The method involves the detection of the mutation in amplified DNA from a patient utilizing probes that span the mutation. Six mutations are identified as being responsible for over 85% of the mutations in the United States population, and a detection kit is described for detecting these six mutations. The methods of this invention can also be used to determine the zygosity of the mutations and to detect the presence of multiple mutations in the GALT gene, both of which are necessary for understanding and counseling heritability and recurrence risks to family members.

DETAILED DESCRIPTION OF THE INVENTION

Definitions:

"GALT" means the enzyme galactose-1-phosphate uridyltransferase.

"Galactosemia" is a deficiency in the level or expression of GALT which results in detectable deviations from normalcy in animals.

As used in the claims, "a" can mean one or more, depending on the context of the claim.

Detailed Description of Invention

The invention described herein involves the use of a group or set of DNA probes to detect mutations in the GALT gene. Prior to this invention, only enzyme activity analyses have been used in clinical screening applications. With the practice of this invention, a rapid and economical screening system for detecting galactosemia in human populations, particularly in newborns, is provided. Based on the discovery of the frequency of the K285N mutation and the existence and frequency of the Y209C mutation, a process for detecting specific mutations in the GALT gene that cause over 85% of the mutations leading to galactosemia currently known in the U.S. population is provided. A preferred embodiment of this invention comprises assaying for the presence of six mutations, listed in Table 1A. In a survey of newborns the prevalence of these mutations is shown in Table 1B. If desired, this process can be followed by additional screening for less common mutations, e.g. listed in Table 2. The process comprises the collection of an RNA- or DNA-containing sample from a patient or a newborn infant, amplification of the DNA (following reverse transcription of the RNA, if needed) that encodes either a portion of or the entire GALT gene, hybridization of the amplified DNA, either serially or in parallel, with each member of a set of detectable probes, each probe being at least 10 nucleotides in length, the set comprising probes having sequences complementary to the sequences set forth in Table 1A, under hybridization conditions that allow only exactly complementary strands to remain as hybrids, and detecting the presence or absence of the hybrids.

TABLE 1A

| Designation# | Sequence* | Approx % found in galactosemic population |
|---|---|---|
| S135L | TGGTTGGAT | 62% of African-American population |
| Q188R | TGCCGGGTA | 70% of white population |
| L195P | TTCCCGCCA | 8% of all ethnic groups |
| K285N | CCAATTATG | 17% of white populations |
| Y209C | GCCTGTAAG | 6–20% of all ethnic groups |
| N314D | CTGGGACCA | 8% of all ethnic groups |
| [deletion] | [absence of signal with any probe] | in Ashkenazi Jewish population |

The number in the designation refers to the amino acid position in the human GALT protein (see, e.g. Leslie et al., ibid., or SEQ ID NO:15). The single lettersor on either side of the number identify the amino acid in the wild-type protein (preceding the amino acid number) and the amino acid present in the mutant protein.
*underlined nucleotide is the one mutated from the wild-type sequence

TABLE 1B

Observed Prevalence In 250 Patients (500 Mutant Alleles)

| Designation | # of Alleles | Percent of Total |
|---|---|---|
| Q188R | 270 | 54.0 |
| S135L | 42 | 8.4 |
| K285N | 24 | 4.8 |
| L195P | 8 | 1.6 |
| Y209C | 6 | 1.2 |
| F171S | 5 | 1.0 |
| [deletion] | 5 | 1.0 |
| Private | 90 | 18.0 |
| Unknown | 50 | 10.0 |
|  | 500 | 100.00 |

TABLE 2

| Designation# | Sequence* | Designation# | Sequence* |
|---|---|---|---|
| A. Missense/Nonsense mutations | | | |
| D28Y | TAC | Q212H | CCG |
| I32N | AAC | L217Pn | CCA |
| Q38P | CCG | L226Pn | CCA |
| V44L | TTG | R231H | CAT |
| V44M | ATG | W249R | AGG |
| R51L | CTC | Y251C | TGC |
| G55C | TGT | Y251Sn | TCC |
| L62M | ATG | R258Cn | TGT |
| R67C | TGC | R259W | TGG |
| L74P | CCG | R262Pn | CCG |
| A81T | ACC | R273G | GGT |
| N97S | AGC | L282Vn | GTC |
| D98N | AAC | L289Rn | CGC |
| D113Nn | AAT | E291K | AAG |
| H114Ln | CTT | E308K | AAG |
| F117Sn | TCC | Q317R | CGG |
| Q118Hn | CAC | Q317Hn | CAT |
| R123G | GGA | H319Q | CAA |
| R123Qn | CAA | A320T | ACT |
| V125An | GCC | Y323H | CAC |
| K127En | GAG | Y323D | GAC |
| C130Yn | TAC | P324S | TCT |
| H132Yn | TAC | P325Ln | CTG |
| T138M | ATG | R328Hn | CAC |
| L139P | CCG | S329F | TTT |
| M142V | GTG | A330V | GTC |
| M142K | AAG | R333W | TGG |
| S143L | TTG | R333G | GGG |
| R148W | TGG | R333Q | CAG |
| R148Q | CAG | K334R | AGA |
| R148Gn | GGG | M336Ln | TTG |
| V150L | CTT | Q344Kn | AAG |
| V151A | GCT | T350A | GCC |
| W154Gn | GGG | Q54Stopn | TAG |
| F171S | TCT | R80Stop | TGA |
| G179D | GAC | W154Stopn | TGA |
| P183T | ACC | R204Stop | TGA |
| H184Qn | CAA | Q212Stop | TAG |
| S192N | AAC | W249Stop | TGA |
| F194L | CTC | L264Stopn | TAG |
| I198Mn | ATG | W316Stop | TAG |
| I198Tn | ACT | E340Stop | TAA |
| A199T | ACC | Q353Stop | TAG |
| R201H | CAT | Y366Stop | TAA |
| E203K | AAG | Q370Stop | TAG |
| Y209S | TCT | | |
| B. Small Insertions/Deletions | | | |
| 528insG | | insG at base 528 | |
| S112fs insA | | insA at base 333 | |
| W134fs delT | | del T at base 400 | |
| ΔC(bp1677)n | | ΔC(bp1677) | |
| L256/P257fs | | at bases 768-770, delete GCC-fs | |
| Δamino acids[n] #260–263 | | Δamino acids #260–263 | |
| ΔT(bp2359)[n] | | ΔT(bp2359) | |
| ΔC(bp2756)[n] | | ΔC(bp2756) | |
| ΔC(bp2782) | | ΔC(bp2782) | |
| L327delC | | base 979, del C-fs | |
| P351fsdelC | | base 1051, del C-fs | |
| 1. Splice Site Mutations | | | |
| 318A → G | | base 318A → G | |
| IVSC | | base 956A → C | |
| IVS3nt + 29G → C | | c.328 + 29 G → C | |
| IVS4nt + 1 | | c.377 + 1 G → C | |
| IVS4nt − 27G → C | | c.378 − 27 G → C | |
| IVS5nt + 62G → A | | c.507 + 62 G → A | |
| IVSFnt1[n] | | base 1472 G → A | |
| IVSF | | base 1631 A → G | |
| IVS7nt + 2 | | c. 687 + 2 T → C | |
| IVS8nt + 13 | | c. 820 + 13 A → G | |
| IVS8nt + 32 | | c.820 + 32 A → G | |

TABLE 2-continued

| | |
|---|---|
| IvS8nt + 58 | c.820 + 58 G → T |
| IVSHnt13 | base 2207 Ab → G |
| IVSJ | C → G |

The number in the designation refers to the amino acid position in the human GALT protein, see Leslie et al., ibid., or SEQ ID NO:15. The single letters on either side of the number identify the amino acid in the wild-type protein (preceding the amino acid number) and the amino acid present in the mutant protein.
*underlined nucleotide is the one mutated from the wild-type sequence
ⁿnovel mutations not previously identified The invention herein described provides the novel mutation, Y209C, in which the amino acid tyrosine is replaced with cysteine at amino acid 209. When a gene carrying the Y209C mutation is analyzed for expression in E. coli, it is scored as a "null" mutation, i.e. there is no significant GALT activity detected. In one embodiment, the invention comprises a process for detecting this mutation in the GALT gene comprising amplifying the GALT gene, or the portion containing exon VII, hybridizing the amplified DNA with a probe at least 10 nucleotides in length that comprises sequence complementary to GCCTGTAAG, and detecting the presence or absence of this hybrid. In one embodiment, the invention comprises a set of probes comprising a probe for the Y209C mutation, as described above, and a probe for at least one other mutation chosen from the groups of mutations listed in Table 1A and Table 2. In another embodiment, the invention provides a set of probes comprising at least one of the novel mutations listed in Table 2 (i.e. those marked with the superscript"ⁿ") and at least one other mutation chosen from the groups of mutations listed in Table 1A and Table 2.

The DNA hybrids produced by the processes of this invention can be detected by any of a number of methods known in the art, e.g. radioactive, chemiluminescent, fluorescent or bioluminescent labeling of the probe, antibody-based detection of a ligand attached to the probe, or detection of double-stranded nucleic acid. Specific examples of labels are digoxigenin, fluorescein, luciferases, and aequorin. Alternatively, the probe can be labeled with biotin and detected with avidin or streptavidin conjugates.

This process can be used to detect carriers of galactosemia, who may themselves be asymptomatic or mildly symptomatic and therefore undiagnosed. Carriers are heterozygous for a mutation, for example one of those listed in Table 1A. Carriers have not previously been identified by the existing screening methods, since they do not demonstrate a significant change in GALT activity.

In a specific embodiment, a portion of the GALT gene comprising exons 5–10 (e.g. nucleotides 1153–2863, GenBank Accession No. M96264; SEQ ID NO: 8) is amplified from the subject's DNA. Alternatively, the GALT gene can be amplified in sections, and the resulting amplicons can be hybridized only with those oligonucleotides carrying a mutation in the amplified region of the gene.

The process of this invention can be used to determine the zygosity of a mutation by hybridizing the amplified DNA to one or more probes comprising the wild-type sequences that correspond, for example, to the mutated sequences listed in Table 1A.

In specific embodiments, the probes used to detect the GALT mutations can be 10, 11, 12, 13, 14, 15, 16, 17, 18, 19, 20, 21, 22, 23, 24, or 25 nucleotides in length.

In a specific embodiment, the probes used to detect the set of mutations, such as the set in Table 1A, are all of the same length, between 10 and 25 nucleotides, and the mutated nucleotide (or the wild-type nucleotide corresponding in position to the location of the mutation) is positioned exactly in the middle of each probe, in the case of probes with an odd number of nucleotides, or, in the case of a probe with an even number of nucleotides, n, the mutation would be located at n/2±1. In such an embodiment, identical hybridization conditions can be used for each probe.

Alternatively, the mutation can be positioned anywhere in the probe that is at least 3 nucleotides from either end of the probe. In using such an alternative approach for detecting a set of mutations, the mutated nucleotide should be in the same position in each probe.

In an alternative embodiment, allele-specific amplification is employed resulting in the amplification of only selected GALT gene alleles. In this embodiment, probes are designed such that the 3' end of one primer is the nucleotide which is mutated (see Blasczyk R, J Wehling et al. 1997 Allele-specific PCR amplification of factor V Leiden to identify patients at risk for thromboembolism, *Beitr Infusionsther Transfusionsmed* 34: 236–41).

In a specific embodiment, tetramethyl ammonium chloride (TMAC) is included in the hybridization buffer, and the reaction is carried out at 55 C. Typically, the temperature of the hybridization is used to discriminate between an exact sequence match and a mismatch, and the temperature at which a given hybrid will "melt", i.e. dissociate into the two complementary single strands, is determined by the length and nucleotide composition of the strands. To minimize the variation in the reaction temperature required to discriminate between the desired exact-match hybrid and the mismatched hybrid, trimethyl ammonium chloride (TMAC) is added to the hybridization buffer. TMAC greatly minimizes the effect of nucleotide composition on the hybridization reaction, so that length of the oligonucleotide becomes the determining factor, which can be easily controlled. Other salts can alternatively be used with similar effects as TMAC (see, for example, Mechior, Jr., WB and P H Von Hippel, 1973, Proc. Natl. Acad. Sci (USA) 70(2): 298–302). In a specific embodiment, probes of 21 nucleotides, with the mutation in the exact middle of the probe, as set forth herein as SEQ ID NO: 1, SEQ ID NO: 2, SEQ ID NO: 3, SEQ ID NO: 4, SEQ ID NO: 5, and SEQ ID NO: 6, are used in the process.

In another embodiment, a kit is provided for use, for example, by diagnostic laboratories in hospitals, clinics or research centers that contains the necessary components to perform a rapid and economical screen for the six most common mutations in the GALT gene. Such a kit comprises a set of probes comprising sequences complementary to the sequences set forth in Table 1A, and a set of amplification primers, complementary to sequences selected from the known sequence of the human GALT gene (e.g. GenBank Accession No. M96264 or SEQ ID NO:7) to amplify the desired portion of or the entire GALT gene in a patient sample. In a specific embodiment, the primers comprise a single pair which amplify a region of the human GALT gene that comprises at least nucleotides 1153–2748 (numbering as in the above-referenced GenBank accession, SEQ ID NO:8). Amplification primers can be 14 to 30 nucleotides in length, although longer ones can also be used.

In another embodiment, the detection method used is an ELISA-based oligonucleotide ligation assay. Probes spanning the various GALT mutations described herein can be divided into a pair of smaller probes or, alternatively, new probe pairs can be designed so that their ends meet within a few base pairs of the mutation (or corresponding wild-type sequence). Such a pair of probes, spanning the sequence of a GALT mutation, are hybridized to the patient's amplified GALT DNA, then ligated, and the probes are then analyzed to determine the presence of a single large probe, which would be the product of the ligation of the perfectly matched pair of smaller probes (see Nickerson, D A, R Kaiser, S. Lappin, J. Stewart, L. Hood, and U. Landegren, 1990, Automated DNA diagnostics using ELISA-based oligonucleotide ligation assay; Proc. Natl. Acad. Sci. USA 87:8923–8927). The absence of a large product indicates the absence of the GALT mutation represented by the pair of probes.

In another embodiment involving a solution-based assay, detection of the GALT gene alleles involves the use of two different labels. For example, the DNA amplification is performed with primers that are labeled with digoxigenin. Multiple alleles can be analyzed by including primers labeled with a different detectable moiety for each allele. The amplified product is melted in solution, and allele-specific probes (as described herein) conjugated with biotin are added to the solution and hybrids are allowed to form. The solution containing these hybrids is added to an ELISA plate coated with avidin or streptavidin to capture the allele-specific hybrids. The hybrids are detected through the presence of digoxigenin.

Throughout this application, various publications are referenced. The disclosures of these publications in their entireties are hereby incorporated by reference into this application in order to more fully describe the state of the art to which this invention pertains.

EXAMPLES

Example 1

A. Oligonucleotides Useful in Detecting GALT Gene Mutations

Oligonucleotides useful in detecting the GALT gene mutation can be synthesized by techniques known in the art. The oligonucleotides can be from nine to twenty-five nucleotides in length; nucleotides shorter than 9 nucleotides will not provide accurate and reproducible results. Nucleotides longer than 25 nucleotides in length for detecting a single mutation in GALT can be used, but they provide no advantages over oligonucleotides 9–25 nucleotides in length. The single nucleotide mutation can be located anywhere in the oligonucleotide, as long as it is at least 3 nucleotides from either end of the oligonucleotide. One set of oligonucleotides of this invention, wherein the mutation is located exactly in the middle of the oligonucleotide, is presented in Table 3.

B. Amplification of DNA

1. GALT Gene PCR

Samples are collected from any tissue or organ of a patient from which RNA or DNA can be amplified. For example, DNA in blood collected and dried onto filter paper can be amplified. Alternatively, a buffy coat fraction from freshly collected blood is preferred for RNA amplification. Patient's DNA or RNA can be amplified in three sections using the following primers:

| Primer Name | Nucleotide Sequence | SEQ ID NO: |
| --- | --- | --- |
| F-S135L | TGT AGT GGC TCT AGC TCT GG | 9 |
| R-S135L | TAT CAG ATA GGG ATA CGG AGC | 10 |
| F-Q188R | GTC AGG AGG GAG TTG ACT TGG | 11 |
| R-Q188R | GCC CTT TTA CAG TTA TCC AGG | 12 |
| F-N314D | TCA AGC AGG GGA TCC TGG GAG | 13 |
| R-N314D | ATC TCT GAA GGT TCA CAC TCC | 14 |

2. GALT Allele-specific Amplification

The presence of a specific GALT mutation or wild type can be detected by using allele specific amplification. A synthetic oligonucleotide, designed to end with a nucleotide that creates the mutation, is used as one of the primers in polymerase chain reaction amplification (for example, see Blasczyk R, J. Wehling et al. 1997 Allele-specific PCR amplification of factor V Leiden to identify patients at risk for thromboembolism, *Beitr Infusionsther Transfusionsmed* 34: 236–41). One or more adjacent nucleotides of the primer may also be modified to increase the discrimination between allele-specific and non-specific hybridization. In addition, this technique can also be used to simultaneously detect multiple mutations. Primers for each of the different GALT alleles are designed to result in differing lengths of the PCR product, or different detectable moieties (e.g. fluorescent molecules, biotin, digoxigenin, or antibody ligands) are attached to the allele-specific oligonucleotide primers.

For example, the following primer sets can be used to detect two specific mutations of this invention. For the mutation S135L, the following primers can be used:

Mutated allele primer: 5' GGT CAT GTG CTT CCA CCC CTG GTT 3'

Wild-type allele primer: 5' GGT CAT GTG CTT CCA CCC CTG GTC 3'

Common reverse primer: 5' CTG CAC CCA AGG GTA CTG GGC ACC 3'

PCR Product=127 base pairs

For mutation Q188R, the following primers can be used:

Mutated allele primer: 5' TTC TAA CCC CCA CCC CCA CTG CCG 3'

Wild-type allele primer: 5' TTC TAA CCC CCA CCC CCA CTG CCA 3'

Common reverse primer: 5° CAA AAG CAG AGA AGA ACA GGC AGG 3'

PCR Product=176 base pairs

The common primer is used in combination with either one of the other primers, the 3' end of which is the specific nucleotide that is different in the mutated allele. The GALT gene DNA from an individual with only the wild-type form of the gene will only produce the appropriately sized product with the wild-type primer and none with the mutated allele primer. A heterozygous individual will produce the appropriately sized product with both primers, and a homozygous individual will not produce any product with the wild-type primer but will yield the appropriately sized product with the mutated allele primer.

C. Hybridization Techniques

When two DNA strands associate through base-pairing, it is referred to as hybridization. Hybridization is strongest when the two strands are exactly complementary. The stability of a hybrid is also a function of temperature, the ionic concentration of the medium, the length of the two strands, and the nucleotide composition, i.e. % A–T or % G–C. Under identical conditions, two strands that are not exactly complementary, differing by even one nucleotide, will be less stable and will disassociate at a temperature at which exactly complementary hybrids remain paired.

This property of mismatched hybrids provides a method to detect mutations in the GALT gene. The GALT sequence in the DNA of the subject, e.g. a newborn or a patient needing a diagnosis, is amplified, using techniques known in the art, such as polymerase chain reaction or cDNA synthesis, to produce copies of the gene which are then immobilized on a support, such as a nylon membrane (see Sambrook, et al.). The DNA on the support is incubated with a solution containing a labeled oligonucleotide from Example 1 at a temperature that promotes formation of hybrids. The support is then washed at a temperature at which only exact hybrids would be stable. The presence of the label is then measured; if the subject's DNA had the mutation corresponding to the oligonucleotide used in the assay, the label would be detected on the support.

Many subjects' DNA can be tested in a microtiter plate format. Additionally, a pool of probes, containing all or a subset of the mutations listed in Table 1A or 1B, can be used simultaneously to make an initial qualitative determination of whether the subject's DNA contains any mutations in the GALT gene. Parallel hybridizations using oligonucleotides for the normal sequence corresponding to the mutated sequence can be performed to determine zygosity. It is also possible to put a unique and distinguishable label on each probe, so that one could determine the presence of different mutations in a single hybridization mixture.

Example 2
GALT Mismatched Hybrids Assay

To use multiple probes in a single hybridization format, an assay was developed by determining an optimal length for the probes so that the same temperature changes would result in the melting of the mismatched hybrids. Oligonucleotides between 9 and 25 nucleotides could satisfy this requirement, and those of 21 nucleotides, with the mutation at position 11, (see table 3) were found to be especially well-suited to a single temperature for disassociation of the hybrid. In addition, the use of tetramethyl ammonium chloride (TMAC) to the hybridization buffer allowed the hybridization temperature to be standardized at 55 C for all probes.

Hybridization Buffers and Techniques:

Amplified DNA in 5 μl aliquots are spotted on a prewetted positively charged nylon membrane, denatured (using 0.5M NaOH, 2.0M NaCl, 25 mM EDTA) and UV-crosslinked. The membranes are prehybridized at 55 ° C. for 30 minutes in a hybridization buffer (3.0M TMAC, 0.6% SDS, 1.0 mM EDTA, 10 mM $Na_3PO_4$, pH 6.8, 5×Denhardt's solution, 40 μg/ml yeast RNA) followed by overnight hybridization in the same buffer and the same temperature containing 1–2 ×$10^6$ cpm/ml $^{32}$P-end labeled oligonucleotides. Unlabeled oligonucleotides corresponding to the normal sequence are used at 10× concentration of the labeled mutant sequence in the hybridization. Similarly, in detecting the normal alleles, unlabeled oligonucleotides corresponding to the mutant sequence are used at 10× concentration of the normal sequence in the hybridization. Filters are then rinsed one time for 20 minutes at room temperature with wash buffer (3.0M TMAC, 0.6% SDS, 1.0 mM $Na_3PO_4$, pH 6.8), then washed again in wash buffer at 55 ° C. for 30 minutes. The membranes are sealed in plastic and set for autoradiography overnight.

TABLE 3

| Mutation | Sequence | Sequence ID NO: |
|---|---|---|
| Y209C | CAGCAGGCCTGTAAGAGTCAG | 6 |
| S135L | CACCCCTGGTTGGATGTAACG | 1 |
| Q188R | CCCCACTGCCGGGTAAGGGTG | 2 |
| L195P | AGCAGTTTCCCGCCAGATATT | 3 |
| K285N | TCTTGACCAATTATGACAACC | 4 |
| N314D | GGCCAACTGGGACCATTGGCA | 5 |

Example 3
Screening of a Galactosemia-Positive Patient for Mutation Type(s)

It is sometimes desirable to determine the exact nature of the mutation or mutations that are contributing to a patient's galactosemia. Such a determination will become critical as gene therapy techniques are implemented to correct these deficiencies. One example for analyzing a single patient's GALT gene for the presence of any or all of the known mutations in the GALT gene is provided herein. Synthetic oligonucleotides carrying each of the mutations to be screened are immobilized individually onto a support, such as a membrane, for example, as "dots" on a nitrocellulose membrane. A sample of the patient's labeled, amplified GALT gene (see Example 1 above for methods of amplification) is hybridized to all the dots on the membrane under conditions that promote only the hybridization of exactly matched sequences. The membrane is washed to remove mismatched and nonspecific hybridizing material, and the membrane is exposed to the appropriate detection system for the label, e.g. film, in the case of a radioactive label, to reveal which synthetic oligonucleotides are hybridizing to the patients' DNA.

Alternatively, detection of a GALT gene mutation can be accomplished in solution, without the need for an immobilization support. An example of a solution-based analysis is the detection of a GALT gene mutation or a wild-type GALT gene by determining the melting temperature of the hybrid of the amplified DNA and the specific oligonucleotide (Ririe, K M, Rasmussen et al. 1997 Product differentiation by analysis of DNA melting curves during the polymerase chain reaction, *Anal Biochem* 245(2): 154–60; Wittwer, C T, M G Herrmann et al. 1997 Continuous fluorescence monitoring of rapid cycle DNA amplification, *Biotechniques* 22(1): 130–1, 134–8). The melting temperature (Tm) of a hybrid is determined empirically by monitoring the absorbance of the solution as the temperature of the solution is raised incrementally. The Tm is typically defined as the temperature at which half of a single hybrid population is melted. When several different hybrids are present in the solution, there will be several different Tm values, representing the melting of each hybrid. The particular Tm value is determined by the G+C content of the hybrids, their length, and the ionic concentration of the solution. Mismatched hybrids will denature at a lower temperature than exactly matched hybrids. One or more of the probes can be hybridized to the amplified DNA and the melting curves of hybrids can be determined against small increments in temperature. Discrimination between multiple mutations can be achieved by using oligonucleotides of differing lengths or by attaching different detectable moieties, such as fluorescent, chemiluminescent, bioluminescent, or radioactive molecules, biotin, or antibody ligands, to the oligonucleotides.

A specific application of this approach, known as fluorescence energy transfer, can be performed using a Lightcycler®, a device manufactured by Roche Diagnostics Ltd., a division of Roche Molecular Biochemicals, Mannheim, Germany (see Wittwer, C T, K M Ririe et al. 1997 The LightCycler®: a microvolume multisample fluorimeter with rapid temperature control. *Biotechniques* 22(1): 176–81). For example, to detect mutation Q 188R, the following primers are synthesized:

Amplification Forward Primer: 5' CTT TTG GCT TAA CAG AGC TCC G 3'

Amplification Reverse Primer: 5' TTC CCA TGT CCA CAG TGC TGG 3'

Anchor probe: 5' GTC CCC GAG GTC ACC CAA AGA ACC G 3'

Detection wild-type probe: 5' GGT GAC GGt CCA TTC CCA CA 3'

Detection mutated allele probe: 5' GGT GAC GGt CCA TTC CCA CA 3'

(The lower case letter represents the nucleotide that is different between the mutated and wild-type alleles). The anchor probe forms one half of the detection probe set and carries a fluorescence quencher. The other half of the probe set has the allele-specific sequence. When the allele specific probe and the anchor probe are hybridized the fluorescence is quenched. Then, during melting at the Tm for the allele specific probe the hybrid melts and fluorescence is observed. In this example, the Tm for the hybrid formed with the wild-type probe is 56 C, while the Tm of the hybrid formed with the mutated allele probe is 65C.

Example 4

ELISA-like Detection of Hybridization

The hybridization of the DNA oligonucleotide probe to the amplified GALT DNA sequences can also be detected using an enzyme-linked immunodetection assay, which can be generally called an ELISA. The amplified DNA is labeled during the amplification reaction with digoxigenin, then hybridized with biotin-labeled probes. Under the hybridization conditions described above, a hybrid of the biotin-labeled probe and the digoxigenin-labeled DNA forms. These hybrids are introduced into avidin-coated microtiter plates, and the biotin-labeled probe is adsorbed to the plate. Digoxigenin-labeled DNA that is hybridized to the bound biotinylated probe is detected using an enzyme-coupled anti-digoxigenin antibodies. Detection signals other than an enzyme can be used to detect the anti-digoxigenin antibodies, as will be recognized by those skilled in the art. Examples of other detection signals include bioluminescent proteins, chemiluminescent or fluorescent labels, or radioactive labels.

Although the present invention has been described with reference to specific details of certain embodiments thereof, it is not intended that such details should be regarded as limitations upon the scope of the invention. The texts of the references herein cited are hereby incorporated in their entirety by reference.

We claim:

1. A process for detecting a mutation in the GALT gene that causes galactosemia, comprising
   (a) amplifying the GALT gene in a patient's genomic DNA,
   (b) hybridizing the amplified DNA with a probe at least 10 nucleotides in length that comprises sequence complementary to GCCTGTAAG, and
   (c) detecting the presence or absence of a hybrid, wherein the presence of the hybrid indicates the presence of a galactosemia-causing mutation.

2. A process for detecting mutations in the GALT gene that cause galactosemia, comprising
   (a) amplifying the GALT gene in a patient's genomic DNA,
   (b) hybridizing the amplified DNA, serially or in parallel, with each member of a set of detectable probes, each probe of the set being at least 10 nucleotides in length, the set comprising probes having sequence complementary to the following sequences: TGGTTGGAT, TGCCGGGTA, TTCCCGCCA, CCAATTATG, GCCTGTAAG, and CTGGGACCA, under hybridization conditions that allow only exactly complementary strands to remain as hybrids, and
   (c) detecting the presence or absence of the hybrids, wherein the presence of one or more of the hybrids indicates the presence of one or more galactosemia-causing mutations.

3. The process of claim 2, further comprising hybridizing the amplified DNA to one or more probes comprising sequences complementary to sequences selected from the group consisting of: TGGTCGGAT, TGCCAGGTA, TTCCTGCCA, CCAAGTATG, CTGGAACCA, and GCCTATAAG, wherein detection of hybrids with one or more of the probes indicates that the patient is heterozyous for the mutation identified in step (c).

4. The process of claim 2, wherein the probes are all of the same length, between 14 and 25 nucleotides, the mutated nucleotide is in the exact middle of the probe, and identical hybridization conditions are used for each probe.

5. The process of claim 4, wherein the hybridization conditions comprise the use of tetramethyl ammonium chloride at 55 C.

6. The process of claim 1, wherein the probe has sequence complementary to the sequence set forth in SEQ ID NO:6.

7. The process of claims 2 or 4 wherein the set of probes comprises probes having sequences complementary to the sequences as set forth in SEQ ID NO: 1, SEQ ID NO: 2; SEQ ID NO: 3; SEQ ID NO: 4; SEQ ID NO: 5; and SEQ ID NO: 6.

8. The process of claim 2, wherein the genomic DNA that is amplified comprises a fragment of the GALT gene from exon 5 through exon 10.

9. The process of claim 2, wherein the presence of the hybrids is detected by measuring detectable moieties attached to the probes.

10. The process of claim 9, wherein the detectable moieties are selected from the group consisting of fluorescent molecules, chemiluminescent molecules, bioluminescent molecules, radioactive molecules, biotin and antibody ligands.

11. A process for detecting mutations in the GALT gene that cause galactosemia, comprising
   (a) amplifying the GALT gene in a patient's genomic DNA,
   (b) hybridizing the amplified DNA, serially or in parallel, with each member of a set of detectable probes, each probe of the set being at least 10 nucleotides in length, the set comprising probes having sequence complementary to the following sequences: TGGTTGGAT, TGCCGGGTA, TTCCCGCCA, CCAATTATG, GCCTGTAAG, and CTGGGACCA, under hybridization conditions that allow both exact and mismatched hybrids to form, and,
   (c) determining the melting temperature of the hybrids formed in (b), wherein the value of the melting temperature indicates whether no, one or more galoctosemia-causing mutations are present.

* * * * *